United States Patent [19]
DiMaio et al.

[11] Patent Number: 5,225,095
[45] Date of Patent: Jul. 6, 1993

[54] FOAM CONCENTRATE

[75] Inventors: Louis R. DiMaio, Wilmington, Del.; Peter J. Chiesa, Jr., Wallace, Calif.

[73] Assignee: Chubb National Foam, Inc., Lionville, Pa.

[21] Appl. No.: 739,648

[22] Filed: Aug. 2, 1991

[51] Int. Cl.$^5$ .............................................. B01J 13/00
[52] U.S. Cl. .................................... 252/307; 252/3; 252/8.05; 252/350; 252/351; 252/352; 252/356; 252/382; 252/314
[58] Field of Search ............... 252/350, 3, 307, 351, 252/352, 382, 8.05, 356, 314

[56] References Cited

U.S. PATENT DOCUMENTS

| | | | |
|---|---|---|---|
| 3,669,898 | 6/1972 | Butler | 252/307 |
| 3,772,195 | 11/1973 | Francen | 252/8.05 |
| 3,929,649 | 12/1975 | Rossiny et al. | 252/3 |
| 4,203,850 | 5/1980 | Wirtz et al. | 252/8.05 |
| 4,209,407 | 6/1980 | Schuierer et al. | 252/3 |
| 4,439,329 | 3/1984 | Kleiner et al. | 252/8.05 |
| 4,594,167 | 6/1986 | Kobayashi et al. | 252/3 |

Primary Examiner—Richard D. Lovering
Assistant Examiner—N. Bhat
Attorney, Agent, or Firm—Anna E. Mack

[57] ABSTRACT

An improved foamable protein hydrolysate based concentrate is provided containing multivalent cations and a water soluble polymer, which remains stable in storage for at least six months and which, when diluted with 10 to 50 parts of water and mixed with air to generate a foam, produces a foam which lasts essentially unchanged for at least three days.

24 Claims, No Drawings

FOAM CONCENTRATE

BACKGROUND

Foaming concentrates based on protein hydrolysate have been known and used since before 1940 for use as fire fighting agents, for crop protection and for a variety of other applications. Frequently, a specific end use application will require a foam which is copious and persistent. Such foams are commonly achieved by the addition of certain metal salts such as those of calcium, zinc, and iron. There are also foaming agents commercially available which produce stable foams persistent for up to several hours. Other ingredients are often added to impart shelf life stability, lower the freezing point, and/or to alter the viscosity.

In order to achieve additional persistence, beyond several hours, water soluble polymers (hydrocolloids) have been added to the concentrate. However, of those few polymers which are effective, most are reactive with the metal ions which are necessarily a part of the formulation. Additionally, the incorporation of a hydrocolloid into the concentrate in a sufficient amount to render the foam persistent for several days (without regard to any interactions with other constituents) increases the viscosity of the concentrate beyond any usefulness. Thus, there is no known prior art protein hydrolysate based foam concentrate containing an effective water soluble polymer which exhibits any practical storage stability. Furthermore, it has been generally regarded by those skilled in such art that a protein hydrolysate concentrate containing multivalent cations and an effective polymer is not practical.

In the past such polymers were premixed in water and added to a foam solution premix of the concentrate just prior to use. After premixing, the concentrate was further diluted for foam production. This two part mixing procedure was inefficient and complex.

For marketing purposes, it is highly desirable to produce a concentrate having the polymer contained therein. Such a product eliminates the end user having to perform the two part mixing procedure. The new concentrate described herein makes it possible to use a one part mixing technique such that the end user need only dilute the concentrate prior to foam production.

Commercially available foam concentrates based on protein hydrolysate are available for use at concentrations ranging from 3% to 6% in water by volume. Such commercial preparations may be used at slightly below or above these ranges depending on the application. The hydrolysates are derived from keratin type proteins which impart the necessary foamability. Collagen or albumin proteins can be cohydrolized or prehydrolized and added later for improved foam stability. Hydrolysis can be accomplished by the use of mineral acids or strong bases, but alkaline hydrolysis with lime has been generally preferred. Subsequent neutralization with sulfuric acid and filtration to remove calcium sulfate renders the clear hydrolysate which may be concentrated to a desired gravity by evaporation. Other desired ingredients are then subsequently added.

Foamability is achieved to a large degree by the formation of surface active complexes by the association of protein liquids with metal cations such as $Ca^{++}$, $Zn^{++}$, $Fe^{++}$, $Fe^{+++}$. There are undisclosed amounts of residual $Ca^{++}$ from the lime hydrolysis but formulations usually have additional ions added to achieve the desired effects. Coupling agents such as glycols, and glycol ethers are often added to enhance foamability. Within the described technology, foams have been made to persist up to 36 hours in some cases.

Other technologies utilizing synthetic surfactants in combinations with hydrocolloids such as polysaccarides are known for producing copious stable foams. But there is no established prior art foam demonstrating foam persistence for several days which can be made available in a practical and stable foam concentrate.

BRIEF DESCRIPTION OF THE INVENTION

For many applications it is desirable to produce a foam which is persistent for several days. Examples of such applications are as temporary covers for landfills and waste piles, covers for spills of hazardous materials and crop protection against frost. Beyond these, there are possibilities for use of a foam which drains its water very slowly or not at all in fire fighting applications such as establishing a fire line in brush fires and forest fires. There also can conceivably be a need for such a foam in industrial applications.

This invention allows production of a practical and stable concentrate which when diluted 10 to 50 times with water can produce a copious and persistent foam which can last at least (3) three days and even beyond (6) six days depending on the mode of application, environmental and climatic conditions. The invention utilizes protein hydrolysate derived from a source of keratin such as hoof and horn meal, chicken feathers, or animal hide. To the hydrolysate is added multivalent metal salts such as ferrous chloride, ferrous sulfate, ferric chloride, ferric sulfate, calcium chloride and/or zinc chloride. To achieve enhanced foam persistence beyond that known in the art, a water soluble polysaccharide polymer is added to the concentrate at a level which normally would render a simple aqueous solution of the polymer so high in viscosity as to be of no practical value. The polymer associates strongly with the other metal ion constituents present in the concentrate.

The combination of the protein hydrolysate, metal salts and the polysaccharide polymer produces foamable concentrates which are highly concentrated, fluid, easily transferred, easily dispersed in water and which generate copious and very persistent foam. Furthermore, these concentrates are stable and storable for up to at least six months.

DETAILED DESCRIPTION OF THE INVENTION

All percentages or parts measurements discussed herein are by weight unless stated otherwise.

The present invention provides a foamable concentrate composition comprising 300 to 900 parts protein hydrolysate, 15 to 60 parts of one or more metal based salts, 5 to 50 parts of a water soluble polymer, 1-30 parts of a known imbibing agent and 10 to 40 parts of a cosolvent in which the polymer is essentially insoluble. The concentrate thus formed remains stable in storage for at least six months and, when diluted with 10 to 50 parts of water, produces a persistent foam which lasts for at least three days.

In the present invention, the foamable concentrate is made from a concentrated solution derived from a hydrolysed protein concentrate base. Such hydrolysed protein bases are well known in the fire fighting foam art. They are produced by hydrolysing keratin containing materials such as animal hooves and horns, fish scales, hair or feathers. Albumen, bloodmeal, dairy derived proteins or proteins from vegetables such as soy bean meal, etc. are other sources of proteinaceous starting materials.

The proteinaceous starting materials may be broken down into peptides, polypeptides and salts of amino acids via alkaline hydrolysis with lime or caustic sodium hydroxide (NaOH). The resulting protein hydrolysate is a major component of the foam concentrate. Other methods for producing the protein hydrolysate may equally well be used.

The protein hydrolysate is commercially available as a 35–50 weight % solids concentrate having a pH from approximately 7 to 8 and a specific gravity of 1.148 to 1.162. It can be obtained from any of a number of manufacturers of protein based fire fighting foam or it may be hydrolyzed, as previously described.

One or more foam stabilizing agents may be added to enhance the bubble stability of the foam. Various foam stabilizing agents are used such as polyvalent metal salts, gums, polysaccharides, soluble starches, starch polymers and deliquescents or humectants. Freezing point depressants such as polyglycols or other glycol ethers may be added in small quantities to retard freezing of the concentrate in colder weather but are not necessary. A concentrate of this mixture is added to water at the time of use, or possibly as much as a few hours before, to produce a foam solution.

The metal based salt is added to the concentrate to provide a level of foam stabilization by bonding the reactive sites on the protein residue, gums or other polyelectrolytes in the formula. Preferred salts are polyvalent and yield cations which complex with protein fragments forming giant surface active species which serve as effective foaming agents. Examples of suitable salts include: calcium chloride, ferrous chloride, ferrous sulfate, ferric chloride, ferric sulfate, ferric ammonium sulfate, magnesium sulfate, magnesium chloride and zinc chloride. Ferrous chloride is the agent of choice as it is relatively inexpensive and is not considered to be environmentally hazardous.

Desirably any number of known freezing point depressants may be added to the basic formulation if needed. In particular, polyalcohols, polyglycol ethers, glycols, etc. Reference to freezing point depressants is only for protection of the concentrate. Hexylene glycol is preferred and is added primarily as a foam booster, although it also serves as a freezing point depressant. Other foam boosters suitable for use include diethylene glycol, dipropylene glycol and glycol ethers such as 2-ethoxyethanol, 2-butoxyethanol and 2-(butoxyethoxy) ethanol.

Preferably, a bactericide is also added as a preservative to prevent the decomposition of the foam concentrate by bacteria. Any number of bactericides may be used such as Kathon, available from Rohm & Haas Co., Nipacide BCP or Nipacide MX available from Nipa Laboratories, and the proportions adjusted according to need. Because protein hydrolysates are excellent nutrient sources for microbiological life forms, a low level toxicity biocide should be added to preserve the concentrate. However, when the concentrate is diluted for use, the concentration of the biocide becomes so small that it can no longer provide the preservative effect. Thus, long term holding of premixed solution is not advised.

Many commercially available dispersants may be optionally added to enhance the dispersion of ingredients and to provide additional foamability and foam stability. Sodium lignosulfonate, sold as Marasperse N-22, available from Daishowa Chemicals is preferred, but others such as alkyl napthalene sulfonates are known in the art and may be employed.

Humectants such as sorbitol, glycerine and sodium lactate may also be added. These agents impart better wind resistance to the foam by keeping the surface of the foam moist longer.

The basic foam concentrate formula is diluted to approximately 2.0 to 3.5% with water prior to turbulation to produce foam. The preferred dilution is approximately 3% but a relatively wide range is functional. At 3% (i.e. 97 parts by volume of water) dilution, the solution produces a high quality foam which is highly cost effective.

To the above basic formula, an additional foam stabilizer may be added to improve the storage shelf life of the concentrate and to improve the long term (measured in days) stability or persistence of the foam after it is applied to a substrate. A number of materials can be used for this purpose. Any known water soluble polymer which develops high pseudoplastic surface viscosities in the foam's lamellae (bubble walls) thus decreasing or eliminating drainage of liquid from the foam would be a suitable additive for enhancing foam persistence. Particularly desirable polymers are hydrocolloids which include water swellable polymers and colloidal materials which yield gel or viscous solution. Still more preferred polymers include polysaccharide polymers which contain sugar units with anionic functionality such as carboxyl or sulfate groups. Some examples of these sugar units are glucuronic acid, pyronic acid, gluconic acid, galactose sulfate and sugar units unique to specific gums. In addition to naturally occurring anionic functionality, synthetically modified polysaccharides are also suitable such as carboxymethyl cellose. Representative examples of suitable water soluble polymers include the following: xanthan gum, algin, welan gum, gellan gum, gum arabic, gum tragacanth, carrageenan, rhamsan gum, carboxymethyl cellulose, polysaccharide PS-7 and modified anionic starches.

Other optional polysaccharides may be added to the foam concentrate to improve foam stability by decreasing drainage, or to make the concentrate more cost effective. Often these polysaccharides act synergestically with the primary polysaccharide to impart better foam stability. These coadditives are non-functional polysaccharides (nonionic) made up of sugar units such as glucose, mannose, anhydroglucose, galactose, rhamnose, and galactopyranose. Synthetically modified anionic polysaccharides to render them non-ionic such as propylene glycol alginate, or cationic such as modified starch also apply. Examples of such optional polysaccharides are guar gum, locust bean gum, hydroxyethyl cellulose, hydroxypropyl cellulose, agar, propylene glycol alginate, scleroglucan and starch.

The addition of the polysaccharide, xanthan gum, commercially available under the trade name Rhodopol 23, manufactured by Rhone-Poulenc, has been shown to increase foam stability and minimize surface erosion of an aging foam blanket. A solution of the basic formulation of the foam concentrate with the addition of a 0.08% portion by weight of xanthan gum may result in an increase in the life of the foam blanket from approximately 48 hours to beyond 72 hours. Suitable ranges of xanthan gum in the foam solution are from roughly 0.03 to 0.1% by weight depending upon the stability of the foam desired. Optimum, foam stability appears to occur with the addition of approximately 0.05 to 0.1% xanthan gum.

Formerly, it was considered necessary to add an aqueous solution of the xanthan gum to a foam solution premix just prior to use, because the addition of anionically functional polysaccharides directly to the concentrate led to precipitation or coagulation. Still further, aqueous solutions of xanthan gum and similar polysaccharides at about 2% or greater concentration have viscosities so high as to lose the fluidity necessary for easy transfer and dispersing during application. Yet, these levels of polymer concentration are necessary for desired performance. Early work demonstrated that foam solution premixes could be made to include the stabilizing gum(s). For example, the preparation of a 550 gallon premix solution which contains 16.5 gallons of foam concentrate such as Terra Foam available commercially from Chubb National Foam, Inc., could also include part of the total make-up water from a 1% xanthan gum or gum solution. Or 45 gallons of a 1% aqueous gum solution is mixed into 505 gallons of water and foam concentrate to yield a 550 gallon batch of foam solution premix. The resulting polymer is 0.08 wt % in this case or roughly 3.65 lbs. of gum in the total volume of foam solution premix. Thus, the combination of the polysaccharide solution premix, and appropriate protein hydrolysate concentrate made possible a high performance and practical protein based foam concentrate for producing foam exhibiting improved stability.

The introduction of a polysaccharide polymer into a protein based foam concentrate is difficult due to the presence of the iron, not the protein. Those gums which are effective for practicing the invention associate strongly with $Fe^{++}$, $Fe^{+++}$, and $Ca^{++}$ (also present) forming precipitate and/or gel. This is ameliorated by the presence of protein fragments (peptides) which serve to complex the iron much the same as chelating agents. The difference is that the peptide/iron complex becomes an effective foaming agent due to polar alignment and the presence of hydrophobic groups on the peptide chains.

The association of gum with iron, which is normally considered to be problematic, is used to advantage in the present invention by ionically encapsulating the gum particle thus limiting its hydration and swelling. It is theorized that the metal ions when associating with the protein liquids orient or polarize the protein-ion complex with respect to hydrophile/hydrophobe domains producing giant complex surface active species. Those are capable of occluding swelling gel particles of polysaccharide (xanthan gum) thus precluding intra-association which would lead to precipitation or gelation, or which otherwise if fully dissolved to form a gel would lead to a very high viscosity solution. Once each hydrated gel particle is surrounded by protective ionic complexes, they remain in stabilized suspension due to ionic repulsion. This allows a stable dispersion of partially hydrated gum with very low viscosity development.

To achieve low viscosity and stable concentrates requires the utilization of an improved mixing technique, wherein the ingredients are added in a preferred order under blending conditions selected to avoid any shearing action deleterious to the formation of a stable suspension. Achieving the desired shelf life stability is accomplished by adding adjuvants capable of acting as imbibing agents and/or cosolvents.

An imbibing agent is a substance which enhances the liquid uptake of a hydrocolloid often resulting in swelling due to the increased volume of the system. Some colloids may also take up a certain amount of liquid without a measurable increase in volume. The imbibing agent permits partial swelling and hydration of the polysaccharide particles and reduces formation of hydrogel (tightly crosslinked polysaccharide). Preferred imbibing or swelling agents are ammonium thiocyanate, urea, thiourea, some of the simple sugars (i.e., dextrose), glycerine, sodium glucoheptonate, sorbitol and other polyhydric alcohols. Some of these agents also function as humectants, such as glycerine, ammonium thiocyanate and urea. Hence, these agents may serve a dual purpose.

The hydrophilic (water-miscible) cosolvent reduces the associative interactions between gum (polysaccharide), protein, and metal ions resulting in lower and more stable viscosities. Preferred cosolvents are N-methyl-2-pyrrolidone, glycerine, propylene carbonate, ethylene glycol, ethylene carbonate, glycol ethers, dimethylformamide, tetrahydrofuran, 2-ethoxyethanol and 2-butoxyethanol.

Some of the adjuvants listed above will be more environmentally attractive than others. Urea and glycerine, in particular, are known to exhibit a low order of toxicity.

The order of the ingredients added and mixing technique are important considerations. It is preferable to first add the metal salt (ferrous chloride) to the protein hydrolysate concentrate before adding the polysaccharide polymer. This allows the complex to equilibrate before the polymer is added. Introducing the polysaccharide before the salt will lead to a viscous mass. It is also preferable to mix the polysaccharide in the cosolvent (N-methyl-2-pyrrolidone) and then add the mixture thus formed to the concentrate. For purposes of this invention, the mixture thus formed will generally be a slurry, defined as a mechanical dispersion of solid polymer particles in a non-solvent (cosolvent) and is prepared as follows. The solid polymer in the form of a powder is added slowly to the non-solvent liquid with sufficient mixing to keep the particles mechanically suspended. The particle size of the powder can be generally between 10 to 200 microns but ideally determined by achieving acceptable concentrate stability and viscosity. The cosolvent should preferably be a water miscible liquid in which the polysaccharide is insoluble or essentially insoluable. This premixing in the cosolvent avoids agglomeration of particles. Hence the cosolvent is acting as a predispersing agent.

Of course, almost any hydrophilic solvent can be used to predisperse the polymer. Water miscible solvents such as alcohols, ketones, esters, amides and nitriles would be useful. Representative examples include: ethanol, propanol, acetone, ethyl acetate, formamide and acetonitrile.

The cosolvent doubles as a predispersant for the polymer. But, for example, if the amount of cosolvent needed in the formula is insufficient to prepare the polymer slurry, then additional solvent of some kind can be used together with the cosolvent. In all cases, a slurry is preferred to adding the polymer dry. If a particular gum were found which did not require a cosolvent in order to make the concentrate stable, then a solvent would still be used to prepare the slurry, but one which also would not upset the system balance.

It is desirable to add the slurry to the concentrate slowly (5 to 15 minutes), but not too slowly to avoid over mixing. Mixing should be of the low shear type (i.e. anchor or gate paddle at low RPM). The RPM will depend on paddle size (10-25 RPM in the production plant, 40-100 RPM in the lab). The objective is to disperse the polysaccharide particles in the concentrate with as little particle to particle contact as possible to encourage ionic encapsulation of individual particles by the metal-protein complex. Shearing encourages hydration and solubilization of the polysaccharide leading to very high viscosities.

EXAMPLE 1

A typical keratin protein hydrolysate is prepared as follows: a mixture by weight of 24 parts lime, 97 parts hoof and horn meal, 10 parts ferrous sulfate, and 1 parts sulfuric acid in 186 parts water is heated to 200° F. for 1 hour in an autoclave. The mixture is allowed to cool and then filtered.

EXAMPLE 2

A foam concentrate is prepared by mixing the protein hydrolysate in Example 1 above with the following ingredients:

| Protein Hydrolysate | 570 parts by wt. |
| --- | --- |
| Hexylene Glycol | 24 " |
| Sodium lignosulfonate | 104 " |
| Ferrous Chloride (29% sol) | 190 " |
| N-methyl-2-pyrrolidone | 18 " |
| Xanthan gum | 25 " |
| Ammonium thiocyanate | 18 " |
| Added Water | 145 |
| Ammonium Hydroxide to adjust ph | 6.8-7.2 |

Best results are achieved by predispersing the xanthan gum in the N-methyl-2-pyrrolidone and adding the predispersion to the mixture after the ferrous chloride, protein hydrolysate and ammonium thiocyanate have been mixed with low shear mixing. The resulting product is uniform and fluid with a typical viscosity of 1500 cps measured with a Brookfield viscometer. Viscosity of xanthan gum in water at the same concentration typically is above 10,000 cps rendering the solution immobile. The xanthan gum solution mixed with a solution of ferrous chloride of similar concentration to that in the above formulation results in formation of irreversible gel.

Samples of the above formulation have been stable for at least six months and have demonstrated stability through three freeze-thaw cycles and three 48 hour heating cycles at 140 F.

A portion of the above foam concentrate was diluted by mixing 3 parts in 97 parts water. The resulting solution was foamed through a 2 gallons per minute foam nozzle at 90 psig air pressure to produce a copious, stiff foam which was collected in a plastic tray to a depth of about 6 inches. The expansion ratio was measured to be about 19. The foam remained virtually unchanged for 3 days and persisted as a continuous blanket for 3 additional days. A commercially available foam concentrate similarly prepared but which excludes xanthan gum, N-methyl-2-pyrrolidone, and ammonium thiocyanate produces a foam which lasts less than 36 hours.

Variations of the foam concentrate formulation described in Example 2 can be prepared by altering the relative amounts of ingredients and/or by replacing them with functionally similar ingredients. Foam concentrates have been prepared with greater and less amounts of N-methyl-2-pyrrolidone and ammonium thiocyanate. Representative examples of alternative formulations include the following:

| Example 3 | |
| --- | --- |
| Protein hydrolysate | 570 parts by wt. |
| Hexylene glycol | 24 " |
| Sodium lignosulfonate | 104 " |
| Ferrous chloride (29% sol.) | 190 " |
| N-methyl-2-pyrrolidone | 18 " |
| Carboxymethyl cellulose (600F TIC) | 25 " |
| Ammonium thiocyanate | 18 " |
| Added water | 145 |
| Ammonium hydroxide to adjust ph | 6.8-7.2 |

| Example 4 | |
| --- | --- |
| Protein hydrolysate | 570 parts by wt. |
| Hexylene glycol | 24 " |
| Sodium lignosulfonate | 104 " |
| Ferrous chloride (29% sol.) | 190 " |
| N-methyl-2-pyrrolidone | 27 " |
| Xanthan gum | 13 " |
| Gum arabic | 12 " |
| Ammonium thiocyanate | 18 " |
| Added water | 145 |
| Ammonium hydroxide to adjust ph | 6.8-7.2 |

| Example 5 | |
| --- | --- |
| Protein hydrolysate | 570 parts by wt. |
| Hexylene glycol | 24 " |
| Sodium lignosulfonate | 104 " |
| Ferrous chloride (29% sol.) | 190 " |
| Glycerine | 27 " |
| Xanthan gum | 10 " |
| Carboxymethyl cellulose | 10 " |
| Sorbitol | 7 " |
| Ammonium thiocyanate | 18 " |
| Added water | 145 |
| Ammonium hydroxide to adjust ph | 6.8-7.2 |

| Example 6 | |
| --- | --- |
| Protein hydrolysate | 570 parts by wt. |
| Hexylene glycol | 24 " |
| Sodium lignosulfonate | 104 " |
| Ferrous chloride (29% sol.) | 190 " |
| N-methyl-2-pyrrolidone | 18 " |
| Xanthan gum | 10 " |
| Starch | 10 " |
| Ammonium thiocyanate | 18 " |
| Added water | 145 |
| Ammonium hydroxide to adjust ph | 6.8-7.2 |

All of the formulation recited in Examples 3-6 generated foams which were stable for at least three (3) days. All of the concentrates used to produce the foams remained stable for at least thirty (30) days and are projected to remain stable for up to six (6) months.

A representative example of an alternate foam concentrate formulation substituting a combination of imbibing agents for the ammonium thiocyanate of the previous examples is the following:

| Example 7 | |
| --- | --- |
| Protein hydrolysate | 570 parts by wt. |
| Sodium glucoheptonate | 22 " |
| Ferrous chloride (29% sol.) | 92 " |
| Sorbitol | 26 " |
| Glycerin | 36 " |
| N-methyl-2-pyrrolidone | 10 " |
| Welan Gum | 20 " |
| Microcrystalline cellulose (4% dispersion in water) | 156 " |
| Ammonium hydroxide to adjust ph | 6.8-7.2 |

The foam generated from the above formulation remained essentially unchanged for at least four days.

A preferred formulation contains the following range of ingredients:

| | % |
|---|---|
| protein hydrolysate | 40-80 |
| ammonium hydroxide | 0-5 |
| hexylene glycol | 0-4 |
| Sodium lignosulfonate | 0-10 |
| ferrous chloride (29% sol) | 6-18 |
| N-methyl-2-pyrrolidone | 1.5-3.5 |
| xanthan gum | 1.5-3.5 |
| ammonium thiocyanate | 1-3 |

A still more preferred formulation contains the following range of ingredients:

| | % |
|---|---|
| protein hydrolysate | 50-60 |
| ammonium hydroxide | 1-2.5 |
| hexylene glycol | 0-3.8 |
| sodium lignosulfonate | 3-9 |
| ferrous chloride (29% sol) | 10-17 |
| N-methyl-2-pyrrolidone | 1.5-3 |
| xanthan gum | 1.5-2.6 |
| ammonium thiocyanate | 1.6-2.2 |

PH is not particularly critical within a reasonably wide working range, but it is desirable to have the concentrate near neutrality to minimize corrosivity. The concentrate will function when it is adjusted within a pH range of about 6.0 to 9.0, but a range of 6.8-7.2 is preferred. A pH too low will lead to precipitation, and a pH too high will lower foamability and foam stability.

Foam concentrates utilizing propylene carbonate in lieu of N-methyl pyrrolidone behaved similarly but slow $CO_2$ off-gasing poses potential problems. Increased levels of N-methyl pyrrolidone increases viscosity build-up, while too low of a level leads to poor storage stability by formation of a gelatinous layer over an exudate. Ammonium thiocyanate or similar imbibing agent is necessary to avoid exudation and separation. Increased levels are useful for lowering viscosity and pour point.

Xanthan gum is a very effective hydrocolloid for slowing down foam drainage and thus making the foam very persistent. As stated earlier herein, other polysaccharides may also be used for this purpose. All or part of the xanthan gum can also be replaced with carboxymethyl cellulose. The level of hydrocolloid used depends on the degree of foam persistence needed for the application.

The additives used in practicing this invention are those which exhibit minimal adverse environmental and toxic effects, and could be replaced by less desirable agents. For example, dimethylformamide can be used in lieu of N-methyl-2-pyrrolidone but is relatively toxic. Thiourea is known to be a good imbibing agent but may be carcinogenic.

Ferrous ion is known to be among the most effective ions for enhancing and stabilizing protein hydrolysate based foam, but it can be partially replaced with ferric, calcium, zinc, and possibly other polyvalent ions.

Thus it is apparent that in accordance with the present invention, an improved foamable concentrate and method of mixing same is provided which fully satisfies the objectives set forth above. While the invention has been described in conjunction with specific embodiments, it is evident that many alternatives, variations, modifications and permutations will become apparent to those skilled in the art in light of the foregoing description. Accordingly, it is intended that the present invention embrace all such alternatives, variations, modifications and permutations as fall within the spirit and broad scope of the appended claims.

What is claimed as new and desired to be secured by Letters Patent is:

1. A foamable concentrate composition comprising 300 to 900 parts protein hydrolysate, 15 to 60 parts of a metal based salt; 5 to 50 parts of a polysaccharide polymer selected from the group consisting of xanthan gum, algin, scleroglucan, welan gum, gellan gum, gum arabic, gum tragacanth, carrageenan, rhamson gum, and polysaccharide PS-7, and a combination of said polymers; 1-30 parts of an imbibing agent; and 10 to 40 parts of a cosolvent in which the polymer is essentially insoluble; which concentrate remains stable in storage for at least six months and which when diluted with 10 to 50 parts of water produces a foam which lasts for at least three days.

2. The composition of claim 1 wherein said metal based salt is selected from the group consisting of calcium chloride, ferrous chloride, ferrous sulfate, ferric chloride, ferric sulfate, ferric ammonium sulfate, magnesium sulfate, magnesium chloride, zinc chloride and a combination of said salts.

3. The composition of claim 2 wherein the imbibing agent is selected from the group consisting of ammonium thiocyanate, urea, thiourea, dextrose, glycerine, sodium glucoheptonate, sorbitol and a combination of said agents.

4. The composition of claim 3 wherein the cosolvent is selected from the group consisting of N-methyl-2-pyrrolidone, glycerine, propylene carbonate, ethylene glycol, ethylene carbonate, glycol ethers, dimethylformamide, tetrahydrofuran, 2-ethoxyethanol, 2-butoxyethanol and a combination of said cosolvents.

5. The composition of claim 4 further comprising a predispersing agent selected from the group consisting of ethanol and propanol.

6. The composition of claim 4 wherein at least a part of the polysaccharide polymer is replaced by a water soluble polymer or water dispersible colloid selected from the group consisting of guar gum, locust bean gum, carboxymethyl cellulose, hydroxyethyl cellulose, hydroxypropyl cellulose, agar, propylene glycol alginate, starch and a combination of said polymers.

7. The composition of claim 6 wherein said polysaccharide polymer or combination of said polysaccharide polymers comprises said cosolvent resulting in an initial mixture, wherein said initial mixture is added to said composition over a time period of about 5-15 minutes.

8. The composition of claim 7 further comprising about 2 to 4% hexylene glycol.

9. The composition of claim 8 further comprising a sufficient amount of ammonium hydroxide to maintain the pH of the concentrate from between about 6 to 9.

10. The composition of claim 9 further comprising a humectant selected from the group consisting of sodium lactate, sorbitol, glycerine and a combination of said humectants.

11. The composition of claim 10 further comprising sodium lignosulfonate.

12. A foamable concentrate composition which remains stable in storage for at least six months and which when diluted with 10 to 50 parts of water produces a foam which lasts for at least three days, comprising the following ingredients in the percentages indicated by weight:

| protein hydrolysate | 40–80 |
|---|---|
| ammonium hydroxide | 0–5 |
| hexylene glycol | 0–4 |
| sodium lignosulfonate | 0–10 |
| ferrous chloride (29% sol) | 6–18 |
| N-methyl-2-pyrrolidone | 1.5–3.5 |
| xanthan gum | 1.5–3.5 |
| ammonium thiocyanate | 1–3 |

13. A method for making a foamable concentrate composition comprising 300 to 900 parts protein hydrolysate, 15 to 60 parts of a metal based salt and 5 to 50 parts of a polysaccharide polymer, which concentrate remains stable in storage for at least six months and which, when diluted with 10 to 50 parts of water and mixed with air to generate a foam, produces a foam which lasts essentially unchanged for at least three days, which method comprises the following steps:
   a) first mixing the metal based salt with the protein hydrolysate; and
   b) combining the mixture obtained in a) above with a suitable imbibing agent prior to adding the polymer.

14. The method of claim 13 wherein said metal based salt is selected from the group consisting of calcium chloride, ferrous chloride, ferrous sulfate, ferric chloride, ferric sulfate, ferric ammonium sulfate, magnesium sulfate, magnesium chloride and a combination of said salts.

15. The method of claim 14 wherein the polysaccharide polymer is selected from the group consisting of xanthan gum, algin, welan gum, gellan gum, gum arabic, gum tragacanth, carrageenan, rhamson gum, scleroglucan and polysaccharide PS-7, and a combination of said polymers.

16. The method of claim 15 wherein the imbibing agent is selected from the group consisting of ammonium thiocyanate, urea, thiourea, dextrose, glycerine, sodium glucoheptonate, and a combination of said agents.

17. The method of claim 16 wherein said polymer is first mixed with a cosolvent in which the polymer is essentially insoluble, and the resulting mixture is then added to the concentrate.

18. The method of claim 17 wherein the cosolvent is selected from the group consisting of N-methyl-2-pyrrolidone, glycerine, propylene carbonate, ethylene glycol, ethylene carbonate, glycol ethers, dimethylformamide, tetrahydrofuran, 2-ethoxyethanol, 2-butoxyethanol and a combination of said cosolvents.

19. The method of claim 18 wherein said polysaccharide polymer is first mixed with a predispersing agent selected from the group consisting of ethanol and propanol, and the resulting mixture is then added to the concentrate.

20. The method of claim 19 wherein at least part of the polysaccharide polymer is replaced by a water soluble polymer or water dispersible colloid selected from the group consisting of guar gum, locust bean gum, carboxymethyl cellulose, hydroxyethyl cellulose, hydroxypropyl cellulose, agar, propylene glycol alginate, scleroglucan, starch and a combination of said polymers.

21. The method of claim 20 wherein about 2 to 4% hexylene glycol is added to the concentrate.

22. The method of claim 21 wherein a sufficient amount of ammonium hydroxide is added to the concentrate to maintain the pH of said concentrate from between about 6 to 9.

23. The method of claim 22 wherein a humectant selected from the group consisting of sodium lactate, sorbitol, glycerine and a combination of said humectants is added to the concentrate.

24. The method of claim 23 wherein about 3 to 9% sodium lignosulfonate is added to the concentrate.

* * * * *